(12) United States Patent
Paliard

(10) Patent No.: US 7,638,679 B2
(45) Date of Patent: Dec. 29, 2009

(54) TOLERANCE AND CHRONIC HEPATITIS C VIRUS

(75) Inventor: Xavier Paliard, San Francisco, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 332 days.

(21) Appl. No.: 09/894,845

(22) Filed: Jun. 27, 2001

(65) Prior Publication Data

US 2002/0068714 A1 Jun. 6, 2002

Related U.S. Application Data

(60) Provisional application No. 60/214,583, filed on Jun. 27, 2000.

(51) Int. Cl.
*C12N 15/00* (2006.01)
(52) U.S. Cl. .................................. 800/21; 800/9
(58) Field of Classification Search .................. 514/44; 800/9, 21
See application file for complete search history.

(56) References Cited

U.S. PATENT DOCUMENTS 6,582,692 B1 * 6/2003 Podsakoff et al. .......... 424/93.2

FOREIGN PATENT DOCUMENTS

WO WO 97/47358 * 12/1997

OTHER PUBLICATIONS

Y Shimizu et al., Journal of Immunology, "Dendritic Cell Immunization Breaks Cytotoxic T Lymphocyte Tolerance in Hepatitis B Virus Transgenic Mice," 1998, 161:4520-4529.*
Ay Lee et al., Hepatology, "Priming of Hepatitis C Virus-Specific Cytotoxic T Lymphocytes in Mice Following Portal Vein Injection of a Liver-Specific Plasmid DNA," 2000, 31:1327-1333.*
Ma Feitelson et al., Journal of Virology, "A Chronic Carrierlike State is Established in Nude Mice Injected with Cloned Hepatitis B Virus DNA," Apr. 1988, vol. 62, No. 4, pp. 1408-1415.*
M Yanagi et al., Proc. Natl. Acad. Sci. USA, "Transcripts from a single full-length cDNA clone of hepatitis C virus are infectious when directly transfected into the liver of a chimpanzee," Aug. 1997, vol. 94, pp. 8738-8743.*
Nakai et al. (Blood, 1998; vol. 91, pp. 4600-4607).*
Caine et al., "Induction of Immunological Tolerance by Porcine Liver Allografts," *Nature* 223:472-476 (1969).
Cantor & Dumont, "Hepatic Suppression of Sensitization to Antigen Absorbed into the Portal System," *Nature* 215:744-745 (1967).
Cerny & Chisari, "Pathogenesis of Chronic Hepatitis C: Immunological Features of Hepatic Injury and Viral Persistence," *Hepatology* 30:595-601 (1999).
Cuison et al., "Schistosome Eggs in the Portal Vein Can Induce Tolerance," *International Journal Parasitology* 25(8):993-998 (1995).

Ehl et al., "Antigen Persistence and Time of T-Cell Tolerization Determine the Efficacy of Tolerization Protocols for Prevention of Skin Graft Rejection," *Nature Medicine* 4(9):1015-1019 (1998).
Gorczynski, "Regulation of IFN-γ and IL-10 Synthesis in Vivo, as Well as Continuous Antigen Exposure, is Associated With Tolerance to Murine Skin Allogrtafts," *Cell Immunology* 160:224-231 (1995).
Kamada et al., "Liver Transplantation in the Rat," *Transplantation* 35(4):304-311(1983).
Kawamura et al., "Transgenic Expression of Hepatitis C Virus Structural Proteins in the Mouse," *Hepatology* 25:1014-1021 (1997).
Koike et al., "Expression of Hepatitis C Virus Envelope Proteins in Transgenic Mice," *Journal of General Virology* 76:3031-3038 (1995).
Millard et al., "Morphological Features of Kidney and Liver Allografts in the Pig," *Transplantation Proc.* 3:505-508 (1971).
Moriya et al., "Hepatitis C Virus Core Protein Induces Hepatic Steatosis in Transgenic Mice," *Journal of General Virology* 78:1527-1531 (1997).
Pasquinelli et al., "Hepatitis C Virus Core and E2 Protein Expression in Transgenic Mice," *Hepatology* 25:719-727 (1997).
Qian et al., "Murine Liver Allograft Transplantation: Tolerance and Donor Cell Chimerism," *Hepatology* 19:916-924 (1994).
Sriwatanawongsa et al., "The Essential Roles of Parenchymal Tissues and Passenger Leukocytes in the Tolerance Induced by Liver Grafting in Rats," *Nature Med.* 1:428-432 (1995).
Starzl, "Acquired Tolerance, Allograft "Acceptance," and Immune Suppression," *Transplant. Proc.* 30:3845 (1998).
Sugiura et al., "Induction of Donor-Specific T Cell Anergy by Portal Venous Injection of Allogeneic Cells," *Immunobiology* 197:460-477 (1997).
Triger et al., "Studies on Hepatic Uptake of Antigen 1. Comparison of Inferior Vena Cava and Portal Vein Routes of Immunization," *Immunology* 25:941-950 (1973).
Wakita et al., "Efficient Cinditional Transgene Expression in Hepatitis C Virus cDNA Transgenic Mice Mediated by the Cre/loxP System," *The Journal of Biological Chemistry* 273:9001-9006 (1998).
Wang et al., "Induction of Specific Allograft Immunity by Soluble Class I MHC Heavy Chain Protein Produced in a Baculovirus Expression System," *Transplantation* 61:448-457 (1996).
Schmidt et al., "Adjuvant Effect of IL-12: Conversion of Peptide Antigen Administration from Tolerizing to Immunizing for CD8+ T Cells in Vivo," *The Journal of Immunology*, 163(5):2561-2567 (1999).
Lee, et al., "Quantification Of The Number Of Cytotoxic T Cells Specific For An Immunodominant HCV-Specific CTL Epitope Primed by DNA Immunization," *Vaccine* 18:1962-1968 (2000).

* cited by examiner

*Primary Examiner*—J. E Angell
(74) *Attorney, Agent, or Firm*—Robins & Pasternak LLP; Roberta L. Robins; Robert J. Gorman

(57) ABSTRACT

This invention provides a model for the induction of immunological tolerance to antigens. The tolerance model of the invention can be used for screening candidate drugs effective in modulating tolerance. The invention also provides the use of such tolerance-modulating drugs as agents for the treatment of chronic illnesses, including chronic viral infections, such as HCV.

10 Claims, 1 Drawing Sheet

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
      NS5a-specific forward primer

<400> SEQUENCE: 1
tgtggagtgg gaccttcccc                                               20

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence:
      NS5a-specific reverse primer

<400> SEQUENCE: 2
tagttcggcg caggaaggg                                                19

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence:  amino acid
      sequence from HCV NS5a protein

<400> SEQUENCE: 3

Ala Gln Ala Leu Pro Val Trp Ala Arg
 1               5

TOLERANCE AND CHRONIC HEPATITIS C VIRUS

CROSS REFERENCE TO RELATED APPLICATION

This application is related to U.S. Provisional Application Ser. No. 60/214,583 filed on Jun. 27, 2000, from which priority is claimed under 37 C.F.R. § 119(e), and which application is incorporated herein by reference in its entirety.

FIELD OF THE INVENTION

The present invention relates to animal models of tolerance to immunogens, for example hepatitis C virus immunogens, and the use of these models for screening for modulators of tolerance. The present invention also relates to the use of such models to screen for agents useful for the treatment of chronic HCV infection and other chronic diseases.

BACKGROUND OF THE INVENTION

Chronic hepatitis C virus (HCV) infection is a serious worldwide health problem. HCV is a positive-strand RNA virus member of the Flaviviridae family (Choo et al., 1989, Science 244:359-362), and is one of the leading causes of chronic liver disease (Tong et al., 1995, N. Engl. J. Med. 332:1463-1466). Additionally, chronic HCV infection has been associated with autoimmune syndromes, immune complex disorders, and mixed cryoglobulinemia (McMurray et al., 1998, Rheum. Dis. Clin. North Am., 24:353-374; Zignego et al., 1999, J. Hepatol., 31:369-376).

One of the most striking features of HCV is its ability, in most instances, to circumvent eradication by the immune system. It is estimated that up to 75% of patients infected with HCV become chronically infected (Tong et al., supra; Alter et al., 1992, N. Engl. J. Med., 327:1899-1905; Heintges et al., 1997, Hepatology, 26:521-526; Seeff, 1995, Semin. Gastrointest. Dis., 6:20-27) despite the fact that most patients generate HCV-specific antibodies (Abe et al., 1992, Hepatology, 15:690-695; Bradley et al., 1990, Gastroenterology, 99:1054-1060; Farci et al., 1992, J. Infect. Dis., 165:1006-1011; Hilfenhaus et al., 1992, J. Gen. Virol., 73:1015-1019; Shimizu et al., 1990, Proc. Natl. Acad. Sci. USA, 87:6441-6444), as well as CD4+ and CD8+ T cell responses (Koziel, 1997, J. Viral Hepat., 4 Suppl. 2:31-41; Koziel et al., 1993, J. Virol., 67:7522-7532; Schupper et al., 1993, Hepatology,18: 1055-1060; Ferrari et al., 1993, Hepatology, 19:286-295). There is evidence, however, that humoral and T cell-mediated immune responses to HCV infection can, at least in some instances, determine the outcome of HCV infection and disease (Zibert et al., 1997, Hepatology, 25:1245-1249; Farci et al., 1996, Proc. Natl. Acad. Sci. USA, 93:15394-15399; Cooper et al., 1999, Immunity, 10:439-449; Missale et al., 1996, J. Clin. Invest., 98:706-714).

In spite of recent progress in the management of chronic HCV disease, the current therapies for chronic HCV infection often do not result in viral clearance (Main et al., 1998, Antivir. Chem. Chemother., 9:449-460; Gish, 1999, Semin. Liver Dis., 19 Suppl. 1:35-47). Several theories have been proposed to explain this lack of clearance including the development of immunological tolerance to HCV antigens (for a review, see Cerny & Chisari, 1999, Hepatology, 30:595-601).

The induction of immunological tolerance in animals is known. The liver is recognized to play an important role in immunological tolerance induction. Cantor & Dumont (1967, Nature 215:744-745) showed that the liver was important to the tolerogenic effect of oral feeding. Introduction of antigens into the portal vein (PV), which leads to the liver, has been shown to induce tolerance. For example, tolerance is induced following PV injection of sheep red blood cells (Triger et al., 1973, Immunology, 25:941-950), schistosome eggs (Cuison et al., 1995, Int. J. Parasitol., 25:993-998), whole allogeneic cells (Gorczynski, 1995, Cell. Immunol., 160:224-231; Sugiura et al., 1997, Immunobiology, 197:460-477), and allogeneic class I heavy chain proteins (Wang et al., 1996, Transplantation, 61:448-457. Shimizu et al. (1998, J. Immunol., 161:4520-4521) studied germline-transmissible, transgenic mouse models of hepatitis B virus (HBV) infection that are tolerant to HBV surface antigen (HBsAg), expressed in the liver from birth.

Although most organ grafts between MHC mismatched individuals are rapidly rejected unless the recipient is immunosuppressed, liver-allografts in various animal species can induce tolerance to themselves and to subsequent allogeneic grafts (Calne et al., 1969, Nature, 223:472-476; Qian et al., 1994, Hepatology, 19:916-924; Sriwatanawongsa et al., 1995, Nat. Med., 1:428-432). In these animal models, tolerance induction occurs after an initial host response against the graft, followed by acceptance (Millard et al., 1971, Transplant. Proc., 3:505-508; Kamada et al., 1983, Transplantation, 35:304-311). There is also clinical evidence that a similar state of unresponsiveness/tolerance by liver grafts is gradually induced in some human recipients (Starzl, 1998, Transplant. Proc., 30:3845). Furthermore, there is an indication from studies in mice that perpetuation of T cell tolerance is dependent on persistence of the tolerizing antigen (Ehl et al., 1998, Nat. Med., 4:1015-1019).

Models for tolerance to HCV have not been developed. A number of HCV germline-transmissible transgenic mouse lines have been developed, expressing different HCV antigens in the liver and other tissues. Koike et al. (1995, J. Gen. Virol., 76:3031-8) developed mice transgenic for the HCV envelope proteins, E1 and E2, under the control of the hepatitis B virus (HBV) regulatory region. Moriya et al. (1997, J. Gen. Virol., 78:1527-31) generated mice transgenic for the HCV core protein, also under the control of the HBV regulatory region. Pasquinelli et al. (1997, Hepatology, 25:719-27) generated transgenic mice expressing the HCV core protein and a carboxy-terminally-truncated E2 protein in the liver, under the control of the liver specific mouse urinary protein and albumin promoters, respectively. Kawamura et al. (1997, Hepatology, 25:1014-21) generated mice transgenic for a cassette of core, E1, and E2 genes, under the control of either the mouse major urinary promoter or the albumin promoter. Additionally, Wakita et al. (1998, J. Biol. Chem., 273:9001-6) developed a germline transgenic mouse, using the cre/lox system, for the inducible expression of HCV proteins (C, E1, E2 and NS2) in the adult animal, to study the immune response to and pathogenesis of HCV infection. All non-inducible germline transgenic HCV models, however, would be expected to be inherently "tolerant" to the particular HCV antigen expressed, as the mice express the proteins at birth and their immune systems see them as "self."

A model of tolerance to HCV that mimics the course of tolerance that develops in the natural progression to chronic HCV status is needed. The present invention is directed to this model of tolerance and other needs.

SUMMARY OF THE INVENTION

This invention provides methods for preparing non-human animals that develop tolerance to a variety of immunogens. These animals can be used to screen for agents that modulate tolerance.

In one aspect of the invention, the immunogen to which tolerance is generated is an immunogen from hepatitis C virus (HCV), and the non-human animals can be used to screen for agents that modulate tolerance to HCV. Preferably, the immunogen is the NS5a protein of HCV. There is sustained expression of the immunogen from a nucleic acid that is delivered to the liver. A variety of methods of delivery of the immunogen-expressing nucleic acid are provided.

The invention also provides methods of screening for agents that modulate tolerance. These screening methods utilize the tolerance models of the invention.

The invention also provides methods of treating a disease associated with tolerance to an immunogen, wherein agents found to modulate tolerance to an immunogen in a non-human animal model of tolerance, are administered to patients suffering from the disease.

The invention also provides methods of treating HCV, wherein agents found to modulate tolerance to HCV immunogens, said agents preferably found in a non-human animal model of tolerance to HCV, are administered to human patients suffering from HCV.

These and other aspects of the invention are more fully described below.

All publications, patents and patent applications cited herein are hereby incorporated by reference in their entirety.

DETAILED DESCRIPTION OF THE INVENTION

Definitions

Figure 1:
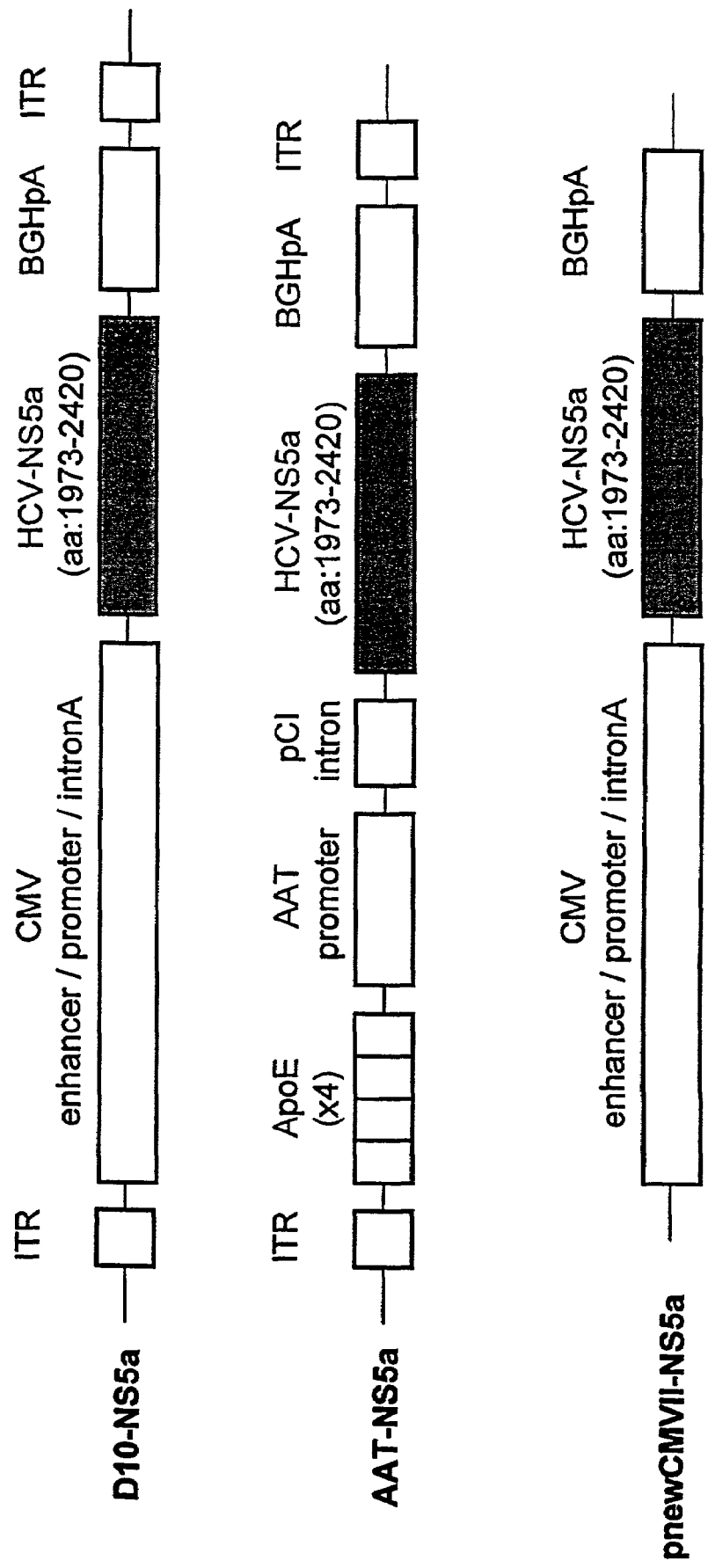
FIG. 1 depicts the HCV NS5a expression plasmids D10-NS5a, AAT-NS5a, and pnewCMVII-NS5a. D10-NS5a and AAT-NS5a are recombinant adeno-associated virus (AAV) vectors, constructed by replacement of the viral capsid gene with the gene of interest, which is, in this case, the HCV non-structural 5a (NS5a) gene. The region containing the promoter/enhancer and gene of interest is bracketed by two AAV inverted terminal repeats (ITRs), which permits D10-NS5a and AAT-NS5a to be packaged into recombinant AAV particles. Further details of the construction of all three vectors are provided in Example 1, below.

Various definitions are made throughout this document. Most words have the meaning that would be attributed to those words by one skilled in the art. Words specifically defined either below or elsewhere in this document have the meaning provided in the context of the present invention as a whole and as typically understood by those skilled in the art.

As used herein, the term "immunogen" refers to any substance that would induce an immune response upon introduction into an animal; that which would be recognized as foreign to the immune system of the animal. "Immunogen" may be used interchangeably with the term "antigen," although "antigen" is more inclusive and defines anything that may be bound by an antibody or T cell receptor. As used herein, "disease-related immunogen" refers to immunogens that are associated with a disease-causing agent. As used herein, immunogen includes viral antigens, preferably any of the proteins of HCV. As used herein, "HCV immunogen" includes any of the proteins of HCV.

As used herein, the terms "sustained expression" or "sustained presence" in reference to an immunogen, are used to distinguish from expression or presence that is transient. Thus, transient expression with DNA vectors that are not stably maintained is not included within the term "sustained expression."

As used herein, the term "exogenously" in reference to delivery of a nucleic acid that directs the expression of an immunogen includes any non-germline delivery.

As used herein, "tolerance" or "tolerant" refers to an immunological state in which the effector cells of the immune system do not respond to an immunogen and do not become activated upon contact with the immunogen. Chronic HCV infection, for example, is included.

As used herein, "patient" refers to human and non-human animals that can be treated with tolerance modulators.

As used herein, "treating" includes the amelioration and/or elimination of tolerance and diseases or conditions associated with tolerance to an immunogen.

As used herein, the term "chronic" in reference to disease includes diseases that persist and are not effectively cleared or resolved.

As used herein, the term "effective amount" refers to the amount required to achieve an intended purpose for treatment without undesirable side effects, such as toxicity, irritation, or allergic response.

As used herein, the term "administering" includes, but is not limited to, transdermal, parenteral, subcutaneous, intramuscular, oral, and topical delivery.

As used herein, the term "agent" in reference to tolerance modulators includes, but is not limited to molecules, compounds, compositions, cellular factors, and cells.

As used herein, "non-human animal" refers to any animal that is not a human and that is amenable to laboratory manipulation, including, but not limited to mammals such as rodents, rabbits, primates and the like, including a mouse, a rat, a guinea pig, or monkey.

As used herein, the terms "modulate," "modulator," or "modulating" in reference to tolerance indicate effecting a change or alteration in the state of immunological tolerance or effecting a change or alteration in the development of immunological tolerance.

As used in this specification and the appended claims, the singular forms "a," "an" and "the" include plural references unless the content clearly dictates otherwise. Thus, for example, reference to "a cell" includes a mixture of two or more cells.

As used herein, the term "comprising" means "including."

Detailed Embodiments

The present invention provides non-human animal models of tolerance that can be used to screen for agents that modulate tolerance. The tolerance models of the invention can be generated by the sustained expression of an immunogen in the liver of the animal. The immunogen may be of viral or bacterial origin, or may any other type of (protein), including, but not limited to, alloantigens, towards which the host animal is not tolerant. The invention is based, in part, on the recognition that the sustained presence of an immunogen in the liver contributes to the generation of a state of immunological tolerance to the antigen. The models of the present invention can be used to investigate the relationship between tolerance induction and chronic disease, as well as to identify agents that can break tolerance and treat chronic disease. More specifically, the present invention provides models of tolerance to HCV immunogens that can be used to identify agents for breaking tolerance to HCV and treating chronic HCV infection.

The practice of the present invention will employ, unless otherwise indicated, conventional methods of virology, immunology, microbiology, molecular biology and recombinant DNA techniques within the skill of the art. Such techniques are explained fully in the literature. See, e.g., Maniatis et al., eds., Molecular Cloning: A Laboratory Manual ($2^{nd}$ ed.) Cold Spring Harbor Laboratory Press, Cold Spring Harbor, N.Y. (1989); Glover, ed., DNA Cloning: A Practical Approach, Vols. I & II; Colowick & Kaplan, eds., Methods in Enzymology, (Academic Press); Weir & Blackwell, eds., Handbook of Experimental Immunology, Vols. I-IV (Blackwell Scientific Pubs.); and Fields & Knipe, eds., Fundamental Virology ($2^{nd}$ ed.) Vols. I & II; Coligan et al., eds., Current Protocols in Immunology, John Wiley & Sons, New York, N.Y. (2000).

Sustained expression or presence of an immunogen must be long enough for the screening of agents, preferably at least about one month in duration. Most preferably, sustained expression or presence means for the life of the animal. Germline transmission of an immunogen, however, is not included.

Any means of delivering a nucleic acid that establishes sustained expression and presence of the immunogen, other than by germline transmission, is contemplated by the present invention. For example, sustained expression can be achieved through the use of viral-based expression vectors that lead to the integration of or stable episomal maintenance of the nucleic acid encoding the immunogen of interest. Many vector systems can be used in establishing sustained expression of an immunogen from a nucleic acid, including, but not limited to, viral/retroviral vectors of alphaviruses, murine leukemia virus (MLV), and feline immunodeficiency virus (FIV).

"Sustained presence" can be achieved by delivering an immunogen in microparticles. For example, an immunogen may be adsorbed to microparticles having an adsorbent surface prepared as described in international application number PCT/US00/03331, filed Feb. 9, 2000, which is incorporated in its entirety by reference.

In a preferred embodiment of the invention, a nucleic acid encoding the immunogen is delivered to the liver packaged within a recombinant adeno-associated virus (AAV) particle. A wide variety of enhancer/promoter combinations can be used in conjunction with the delivery vectors to achieve sustained expression of the immunogen.

In preferred embodiments of the invention, the nucleic acid encoding the immunogen is under the control of the human cytomegalovirus (hCMV) enhancer/promoter or under the control of a hybrid construct of the human apolipoprotein E (ApoE) enhancer and the human alpha-1 anti-trypsin (AAT) promoter. The hCMV immediate early region (IE1) with intron A has been shown to be a potent promoter of expression of heterologous genes in mammalian cells (Chapman et al., 1991, Nucleic Acids Res. 19:3979-3986). The hybrid ApoE/AAT enhancer/promoter yields high levels of expression from liver cells (Okuyama et al., 1996, Hum. Gene Ther. 7:637-645), and its construction is described in international application number WO 98/00542, published Jan. 8, 1998, which is incorporated in its entirety by reference. More preferably, the route of delivery to the liver is by administration through the portal vein (PV). Portal vein delivery of recombinant adeno-associated virus (AAV) particles, in which the transgene is under the control of either the ApoE/AAT enhancer/promoter or the CMV enhancer/promoter, results in sustained gene expression (>6 months) in the liver of injected mice (W. Manning, unpublished data).

In a more preferred embodiment of the invention, a gene coding for the immunogen is cloned into an expression construct containing AAV inverted terminal repeats (ITRs), to permit packaging in AAV particles for delivery to the liver. In further preferred embodiments of the invention, recombinant AAV plasmid constructs, containing the HCV NS5a gene, and AAV ITRs are packaged into AAV particles for delivery to the liver.

In another preferred embodiment of the invention, a model of tolerance to HCV is generated by PV injection, in mice, of recombinant AAV particles that direct the sustained expression of a HCV immunogen in the liver. In a more preferred embodiment of the invention, the immunogen is the NS5a protein of HCV. This model can be used for the analysis of the immunology and pathogenesis of chronic HCV infection, and for testing and developing strategies to treat chronic HCV infection.

Induction of humoral and cell-mediated immune responses to an immunogen can be measured in a variety of ways known to those of skill in the art. Antigen-specific antibody generation may be demonstrated by methods which include enzyme-linked immunosorbent assay (ELISA), radioimmunoassay, immunoblotting, and immunofluorescence. Antigen-specific T cell responses may be examined by methods which include cytotoxic T lymphocyte (CTL) assay, analysis of activation markers by flow cytometry, tetrameric MHC staining, intracellular staining for various factors (such as cytokines and perforin), cytokine secretion analysis, and lymphoproliferation assay (LPA). The use of MHC-class I-peptide tetramers to directly visualize antigen-specific CD8 cells by flow cytometry allows a more precise quantification of the full complement of antigen-specific cells. Enzyme-linked immunospot (ELISPOT) assays can be used to quantify T cell responses by the detection of cytokine secretion. Detailed protocols for interferon-γ (IFN-γ) ELISPOT assay, tetrameric MHC class I-peptide and flow cytometry analyses, as applied to human immune responses to HCV, are provided in Lechner et al., 2000, J. Exp. Med. 191:1499-1512, which is incorporated in its entirety by reference.

Tolerance at the T cell level means that T cells are not activated and do not respond when contacted with the immunogen or with antigenic portions of the immunogen. T cell tolerance can be due to 1) anergy, where antigen-specific T cells are present, but no longer respond; 2) elimination of such antigen-specific T cells; or 3) some other mechanism. Tolerance can be demonstrated by a variety of immunological assays including, for example, the cytotoxic T lymphocyte assay, which detects the antigenic responsiveness of CTLs present in a population of cells.

Other assays of immune function, including mixed lymphocyte reactions and cytokine analyses, may be used to determine immune cell responsiveness and status of tolerance. Many such assays are known to the art. For example, cytokine levels may be determined. Levels of cytokines, such as IL-2, IL-4, IL-10 and IFN-gamma present in cell free culture supernatants ($10^6$ cells per ml in the presence or absence of specific proteins) from various time points are determined by specific ELISA (R&D Systems or Endogen) following the manufacturer's specifications.

In preferred embodiments of the invention, the non-human animal is a vertebrate, more preferably, a non-human primate. For example, it is contemplated that the methods of the present invention can be carried out with chimpanzees. Analyses of immune responses and induction of tolerance in chimpanzees can be carried out using any of the aforementioned immunological protocols. Immune responses to HCV in the chimpanzee have been examined by Cooper et al., supra.

HCV infects the liver, and can lead to chronic HCV infection. Such chronic HCV infection suggests a lack of clearance by the immune system. HCV infection generates HCV-specific T cells, which can be isolated from HCV-infected humans and chimpanzees (Cooper et al., supra. One can postulate, that such HCV-specific T cells, or at least a portion of them, may become tolerant (e.g., by deletion, anergy, or some other mechanism), contributing to the chronic infection.

Generally, T cells become primed, i.e., activated, upon contact with immunogen. If the balance between priming and tolerization of HCV-specific T cells is in favor of priming, the infected individual will resolve the acute HCV infection. If, on the other hand, the balance leans towards immunological tolerance to the immunogen, chronic HCV infection will be established. When sustained expression of HCV non-structural 5a (NS5a) protein was established in the liver in mice, T cells specific for NS5a were tolerized.

Thus, a factor in inducing a state of tolerance is "sustained expression" or long-term presence of the immunogen in the liver. The expression of or presence of the immunogen in the liver should be durable in time. Even when tolerance is achieved, however, there is always an initial phase of priming to the immunogen. After that initial priming phase, if there is sustained expression of the immunogen in the liver, tolerance can be induced and demonstrated.

When only priming occurs, the antigen-specific cytotoxic T lymphocytes remain responsive, and such responsiveness can be demonstrated in a classic $^{51}Cr$ release assay. However, with sustained expression of the immunogen in the liver, tolerance is established. The inventors herein have demonstrated that sustained expression in the mouse and rat liver of the immunogen NS5a protein of HCV results in the induction of tolerance. Specifically, following an initial portal vein injection of NS5a-expressing AAV particles, two intramuscular boosts with NS5a-expressing "naked" DNA (DNA vaccination) failed to prime NS5a-specific T cells, as evidenced by a lack of NS5a-specific CTL response in the $^{51}Cr$ release assay. This model of tolerance provides a system to test various strategies to break this state of tolerance.

It is contemplated that the models of the present invention can be used for the analysis of the promotion, the breaking, and the prevention of tolerance, i.e., modulation of tolerance. The modulation of tolerance can be detected in a wide variety of assays known to the art, including, but not limited to, the $^{51}Cr$ release assay.

The present invention, therefore, provides models of tolerance and methods of using these models to discover agents that prevent, break, or promote tolerance as well as agents that may enhance a tolerant state. Those of skill in the art will appreciate that tolerance modulators that prevent or reverse tolerance will be useful to the treatment of diseases having a tolerance component, including, but not limited to, chronic HCV infection, other microbial or parasitic infections, and cancer. Those of skill in the art will also appreciate that tolerance modulators that promote tolerance induction or strengthen a state of tolerance will be useful in the development of improved transplantation technologies and for the treatment of autoimmune diseases and allergic reactions.

Although individual needs may vary, the determination of optimal ranges for effective amounts of formulations is within the skill of the art. Human doses can also readily be extrapolated from animal studies (Katocs et al., Chapter 27 In: *Remington 's Pharmaceutical Sciences*, 18$^{th}$ Ed., Gennaro, ed., Mack Publishing Co., Easton, Pa., 1990). Generally, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s)(Nies et al., Chapter 3 In: *Goodman & Gilman's The Pharmacological Basis of Therapeutics,* 9$^{th}$ Ed., Hardman et al., eds., McGraw-Hill, New York, N.Y., 1996). A dosage in the range of about 5 to 100 μg is contemplated.

A common requirement for any route of administration is efficient and easy delivery. In one embodiment of the invention, the agents are administered orally. In a preferred embodiment, the agents are administered intramuscularly. Other means of administration include, but are not limited to, transdermal, transcutaneous, subcutaneous, intraperitoneal, mucosal, or general persistent administration.

Compositions used for treating diseases associated with tolerance comprising a tolerance modulator and a pharmaceutically acceptable carrier may be formulated by one of skill in the art with compositions selected depending upon the chosen mode of administration. Suitable pharmaceutical carriers are described in *Remington's Pharmaceutical Sciences*, supra.

Many agents have already been shown to be effective in modulating tolerance in various systems. Additionally, various immune effector molecules have been implicated as targets for modulation of tolerance. The following references relate to the use of various agents and/or the targeting of a variety of immune effector molecules to modulate tolerance: Ushio et al., 1998, J. Immunol., 160:2080-2088; Shimizu et al., 1998, supra.; Qian et al., 1998, Transplantation, 65:1590-1598; Donckier et al., 1998, Eur. J. Immunol., 28:1426-1430; Scheper et al., 1996, Ann. N.Y. Acad. Sci., 795:403-409; Schwarz et al., 1996, J. Invest. Dermatol., 106:1187-1191; Becker & Brocker, 1994, Exp. Dermatol., 3:283-289; Flamand et al., 1998, J. Immunol., 160:4666-4669; Sotomayor et al., 1999, Nat. Med., 5:780-787; Li et al., 1999, J. Immunol., 163:2500-2507; Schmidt & Mescher, 1999, J. Immunol., 163:2561-2567; Seibert et al., 1999, Nat. Med., 5:621-622; Ferguson & Green, 1999, Nat. Med., 5:1231-1232; Diehl et al., 1999, Nat. Med., 5:774-779; Li et al., 1999, Nat. Med., 5:1298-1302; Wells et al., 1999, Nat. Med., 5:1303-1307; Newberry et al., 1999, Nat. Med., 5:900-906; Morteau, 1999, Nat. Med., 5:867-868.

The agents that have been used in other settings for modulating immunological tolerance can be tested in the tolerance models of the present invention for ability to prevent or break tolerance in these models. For example, agents can be screened for their ability to prevent or break tolerance to HCV immunogens. Such agents are expected to be useful in the treatment of chronic HCV. For example, without limitation thereto, antibodies to CD40, CD80, CD86, and Fas; cells, including, but not limited to, dendritic cells and macrophages; cellular factors, including, but not limited to, IL-2, IL-6, IL-10, IL-12, TGFβ, and Flt-3 ligand; pharmaceuticals, including, but not limited to, cyclosporin A; and other agents, including, but not limited to, COX-2 inhibitors, can be tested in the models of the present invention for their ability to modulate HCV.

This invention also provides the use of such agents to treat other conditions and chronic diseases in which immunological tolerance is involved. Such diseases include, but are not limited to, microbial or parasitic infections (for example, malaria), and cancer.

This invention also provides the use of any tolerance model, including, but not limited to transplantation-and peptide-induced tolerance models, to screen for tolerance modulators, that can be used for the treatment of chronic HCV disease, in particular, or other chronic diseases, including, but not limited to HBV, cancer, and malaria. For example, the invention also provides the use of chronically HCV-infected non-human animals, e.g., chimpanzees, to screen for tolerance modulators. Potential tolerance modulators include, but are not limited to, biological factors, cells, and pharmaceuticals.

Any of the aforementioned agents could be used alone, in combination with a therapeutic vaccine, in combination with anti-microbial/viral therapy, or in combination with any other agent shown to be useful for the treatment of the aforementioned diseases.

Other embodiments of the invention will be readily understood by those of skill in the art.

The invention is further illustrated by way of the following examples, which are intended to elaborate several embodiments of the invention. These examples are not intended to, nor are they to be construed to, limit the scope of the invention. It will be clear that the invention may be practiced otherwise than as particularly described herein. Numerous modifications and variations of the present invention are possible in view of the teachings herein and, therefore, are within the scope of the invention.

EXAMPLES

Example 1

Materials and Methods

Peptides p214K9 is an immunodominant, $H-2^k$-restricted, HCV-1a-NS5a-specific CTL epitope peptide. The p214K9 peptide contains a nine amino acid stretch (residues 2152 through 2160) of HCV NS5a protein. Peptide p214J was used as an NS5a-derived control peptide. Peptides p214K9 and p214J are described in further detail in Lee et al., 2000, Vaccine, 18:1962-1968. Peptides were synthesized using Fmoc solid phase methods by Research Genetics (Huntsville, Ala.).

Cell Lines

The fibroblast cell lines L929 ($H-2^k$) and SvBalb ($H-2^d$), used as targets in cytotoxic T cell assays, express class I but not class II major histocompatibility complex (MHC) molecules. Cells lines that are used to test vectors for protein expression include the human kidney cell line 293 and the hepatoblastoma cell line HepG2 (both from ATCC).

Mice

C3H/HeJ ($H-2^k$) mice (Jackson Laboratories) were housed in a pathogen-free environment. All experimental mice were females and were used between 7 and 11 weeks of age.

Example 2

Generation of the Vectors

Schematic representations of two recombinant adeno-associated virus (AAV), HCV non-structural 5a (NS5a) expression constructs and one NS5a expression vector are presented in FIG. 1.

The cytomegalovirus (CMV)-driven expression plasmid, D10-NS5a, was constructed by cloning the CMV enhancer/promoter/intron A/bovine growth hormone (BGH) poly A signal expression cassette from pKm201 (Manning et al., 1998, Hum. Gene Ther., 9:477-485) between the AAV inverted terminal repeats (ITRs) of the AAV vector pD10 (Wang et al., 1997, J. Virol., 71:3077-3082). The liver-specific plasmid, AAT-NS5a, was constructed by cloning, in order, four copies of the 154 bp human apolipoprotein E (ApoE) enhancer (Shachter et al., 1993, J. Lipid Res., 34:1699-1707), the human alpha-1 anti-trypsin (AAT) promoter (−350 to +50)(Long et al., 1984, Biochemistry, 23:4828-4837), the chimeric intron from pCI (Promega, Madison, Wis.), a polylinker, and the BGH poly A signal, between the AAV ITRs of pD10. Both the ApoE enhancer element and the AAT promoter were amplified from human genomic DNA (Promega). The HCV-NS5a gene was introduced into each vector by cloning the full length HCV-NS5a gene (coding for HCV amino acid residues 1973-2420, with introduction of a Met at position $Ser_{1973}^{-1}$ and a stop codon at position $Cys_{2420}^{+1}$) from HCV-1a (Choo et al., 1991, Proc. Natl. Acad. Sci. USA, 88:2451-2455) into the polylinker sites. Vectors D10-NS5a and AAT-NS5a, packaged as AAV viral particles for injections, are referred to as AAV-CMV-NS5a and AAV-AAT-NS5a, respectively, in Table 1, infra.

The pnewCMVII-NS5a plasmid (Lee et al., supra) is equivalent to the D10-NS5a plasmid, but does not contain the two AAV ITRs, and cannot be packaged in AAV particles. This vector is used for "naked" DNA injections and is referred to as NS5a-DNA in Table 1, infra.

Control vectors, useful for demonstrating proper delivery, were constructed by cloning the luciferase gene (Promega) into the polylinker rather than the NS5a gene. Many other reporter genes known to the art can be used for such control vectors. All plasmid DNAs were purified using Qiagen endotoxin-free kits (Qiagen, Chatsworth, Calif.).

In Vitro Gene Expression

Proper functioning of the regulatory control elements of the D10-NS5a and AAT-NS5a vectors was assessed in vitro following transient transfections of cell lines of different tissue origin. 293 (kidney) cells and HepG2 (liver) cells were mock transfected (control) or transiently transfected in the presence of LT-1 (Mirus, Madison, Wis.), according to the manufacturer's specifications, with 1 μg of D10-NS5a or AAT-NS5a plasmid DNA. After 48 hours, cells were lysed in 1xNP-40 lysis buffer in the presence of a protease inhibitor cocktail (Boehringer-Mannheim, Indianapolis, Ind.), and expression was analyzed by Western Blot using the mouse anti-HCV-NS5a-specific monoclonal antibody 2F9-1/D7 (ascites; 1:500), followed by a goat anti-mouse antibody labeled with POD (Boehringer-Mannheim; 1:20,000). Detection was performed by ECL (Amersham-Pharmacia, Piscataway, N.J.). The results indicated that, as expected, the D10-NS5a plasmid expressed NS5a in both cell lines, but the liver-specific AAT-NS5a plasmid only expressed NS5a in the HepG2 cells.

Example 3

Generation of Mouse Model—Immunization Protocol

C3H/HeJ (H-$2^k$) mice were immunized by intra-muscular (IM) or portal vein (PV) injection with $10^{11}$ recombinant AAV particles. PV injections were carried out using a 30-gauge ½ inch needle and a 1 ml syringe over a 30 second period, while a Kleinert-Kutz microvessel clip was applied at the junction of the hepatic vein and the caudal vena cava as described (Zhang et al., 1997, Hum. Gene Ther., 8:1763-1772), with $5 \times 10^{11}$ viral particles in a saline solution containing 15% mannitol (Sigma, St Louis, Mo.) and 2.5 U/ml heparin (Elkins-Sinn, Cherry Hill, N.J.). For IM injections, a total of $1 \times 10^{11}$ recombinant AAV particles, in 100 µl saline, were injected in the tibialis anterior (TA) muscles (50 µl into each muscle). The initial injection is indicated as "$1^{St}$" immunization in Table 1.

Two groups of mice received initial injections of recombinant AAV particles where the CMV promoter drives NS5a expression (D10-NS5a). These groups are represented in Table 1 by individual mice, numbers 751 and 766, that received IM and PV injections, respectively. Recombinant AAV particles containing D10-NS5a are referred to as AAV-CMV-NS5a in Table 1. Two groups of mice received injections of recombinant AAV particles where the AAT enhancer drives NS5a expression (AAT-NS5a). These groups are represented in Table 1 by individual mice, numbers 757 and 775, that received IM and PV injections, respectively. Recombinant AAV particles containing AAT-NS5a are referred to as AAV-AAT-NS5a in Table 1. Control mice (represented in Table 1 by mouse number 3) received no initial injections. Method of injection (IM or PV) or status as control (N/A) is indicated in Table 1 under the column labeled "Rte."

Mice were boosted with IM injections at four weeks and again at eight weeks post initial injection. Boost injections were carried out with 100 µg of pnewCMVII-NS5a plasmid DNA, in 100 µl saline (50 µl into each TA muscle). In Table 1, these boosts are indicated as the "$2^{nd}$" and "$3^{rd}$" injections in the "Immunization" column, and plasmid pnewCMVII-NS5a is referred to as "NS5a-DNA."

Example 4

Demonstration of Induction of Tolerance—Intracellular Staining for IFN-γ

Mice were sacrificed 12 days after the final boost following the immunization protocol of Example 3. After lysis of the red blood cells, spleen cells from individual mice were cultured in media alone or restimulated ex vivo with 2 µg of the immunodominant HCV NS5a-specific, CTL epitope peptide, p214K9, for 6 to 12 hours in culture media (50% RPMI 1640 and 50% alpha-MEM, 10% heat-inactivated fetal bovine serum (FBS), $5 \times 10^{-5}$ M 2β-mercaptoethanol and 1% antibiotics) containing 50 U/ml of rIL-2 (Chiron) and 3 µM monensin (Pharmingen). Splenocytes were stained according to Pharmingen's protocol for surface CD8 with fluorescein isothiocyanate (FITC)-conjugated anti-mouse CD8 (Pharmingen), and for intracellular IFN-γ with phycoerythrin (PE)-conjugated anti-mouse IFN-γ (Pharmingen). Cells were analyzed on a FACScalibur. The number of events acquired was such that at least 10,000 CD8+ cells were acquired for each sample. Data files were analyzed using the CellQuest software. The results are presented in Table 1. The values presented in Table 1 for % of CD8+ cells that are also IFN-γ+ have been corrected for background IFN-γ secretion by those cells not restimulated with peptide prior to FACS analysis.

Example 5

Demonstration of Induction of Tolerance—$^{51}$Cr Release Assay of HCV-NS5a-Specific CTLs Spleen cells from immunized animals were cultured at $5 \times 10^6$ cells per well in 2 ml of medium (50% RPMI 1640 and 50% alpha-MEM, 10% heat-inactivated fetal bovine serum, 5 $\times 10^{-5}$ M 2-mercaptoethanol and 1% antibiotics) supplemented with 2% interleukin-2-containing supernatant (Rat T-STIM, Collaborative Biomedical Products, Bedford, Mass.). Of those cells, $1 \times 10^6$ were sensitized with 1 µM of peptide (p214K9) for one hour at 37° C., washed, and added to the remaining $4 \times 10^6$ untreated spleen cells. Cultures were assayed for cytotoxic activity at day 6 against peptide-sensitized (1 µM for 1 hour), $^{51}$Cr-labeled L929 ($H-2^k$) target cells in a standard $^{51}$Cr release assay (Doe et al., 1996 Proc. Natl. Acad. Sci. USA 93:8578-8583). SvBalb ($H-2^d$) cells are were used as control targets. L929 and SvBalb cells express class I but not class II major histocompatibility complex (MHC) molecules. In some experiments, unlabeled target cells (cold targets) are added to the assay. Percent specific lysis was calculated as follows:

100×(mean experimental release−mean spontaneous release) (mean maximum release−mean spontaneous release).

Results are shown in Table 1 for an individual mouse in each group. The results indicate that HCV-NS5a-specific CTLs are tolerized following PV injection of AAV particles, but not following IM injection of either AAV particles or "naked" (unpackaged) plasmid DNA.

TABLE 1

| | | | Intracellular Staining | $^{51}$Cr release Assay | | |
|---|---|---|---|---|---|---|
| Mouse # | Immunization | Rte | % CD8+ cells IFN-γ+ | E:T ratio | L929/- | L929/p214K9 |
| 751 | $1^{st}$: AAV-CMV-NS5a | IM | 0.43 | 60:1 | 2 | 76 |
| | $2^{nd}$: NS5a-DNA | IM | | 20:1 | <1 | 61 |
| | $3^{rd}$: NS5a-DNA | IM | | 7:1 | <1 | 35 |
| 757 | $1^{st}$: AAV-AAT-NS5a | IM | 0.25 | 60:1 | 5 | 49 |
| | $2^{nd}$: NS5a-DNA | IM | | 20:1 | <1 | 22 |
| | $3^{rd}$: NS5a-DNA | IM | | 7:1 | <1 | 9 |

TABLE 1-continued

| Mouse # | Immunization | Rte | Intracellular Staining % CD8+ cells IFN-γ+ | $^{51}$Cr release Assay E:T ratio | L929/- | L929/p214K9 |
|---|---|---|---|---|---|---|
| 766 | 1$^{st}$: AAV-CMV-NS5a | PV | <0.01 | 60:1 | 2 | 2 |
|  | 2$^{nd}$: NS5a-DNA | IM |  | 20:1 | <1 | 1 |
|  | 3$^{rd}$: NS5a DNA | IM |  | 7:1 | <1 | <1 |
| 775 | 1$^{st}$: AAV-AAT-NS5a | PV | <0.01 | 60:1 | 5 | 6 |
|  | 2$^{nd}$: NS5a-DNA | IM |  | 20:1 | 2 | 2 |
|  | 3$^{rd}$: NS5a-DNA | IM |  | 7:1 | <1 | <1 |
| 3 | 1$^{st}$: Nothing | N/A | 0.47 | 60:1 | 8 | 68 |
|  | 2$^{nd}$: NS5a-DNA | IM |  | 20:1 | 3 | 58 |
|  | 3$^{rd}$: NS5a-DNA | IM |  | 7:1 | 3 | 40 |

The data are presented for representative mice from groups that were treated under various conditions. The mouse designation numbers are provided in the first column. The second column provides the immunization protocol used for each group of mice. AAV-CMV-NS5a and AAV-AAT-NS5a refer to AAV viral particles containing the vectors D10-NS5a and AAT-NS5a, respectively. NS5a-DNA refers to the vector pnewCMVII-NS5a used as "naked" DNA. The third column provides the route (Rte) of each injection, either intramuscular (IM) or portal vein (PV). The fourth column provides the percentage of CD8+ cells that are also intereron-gamma (IFN-γ)+. The last three columns provide data from $^{51}$Cr release assays, i.e., the effector cell (splenocyte) to target cell (E:T) ratio, the percentage $^{51}$Cr release for unsensitized target cells, and the percentage $^{51}$Cr release for peptide-sensitized target cells, respectively. Tolerance is demonstrated for mice numbers 766 and 755.

Example 6

Induction of Tolerance in Rat

DA rats were immunized by portal vein (PV) injection with 10$^{12}$ AAV-AAT-NS5a recombinant AAV virions, described above, or with 400 μg of "naked" DNA (plasmid pnewCMVII-NS5a), also described above. Rats were boosted with IM injections of pnewCMVII-NS5a 13 weeks post initial injection. Four weeks later, animals were challenged IP with 5×10$^7$ pfu of a vaccinia virus vector including the coding sequence for full-length NS5a. Animals were sacrificed 5 days later.

After lysis of the red blood cells, spleen cells from individual rats were cultured in media alone or restimulated ex vivo with 2 μg of p227Kb for 6 to 12 hours in culture media (50% RPMI 1640 and 50% alpha-MEM, 10% heat-inactivated fetal bovine serum (FBS), 5×10$^{-5}$ M 2β-mercaptoethanol and 1% antibiotics) containing 50 U/ml of rIL-2 (Chiron) and 3 μM monensin (Pharmingen). The p227Kb peptide is an HCV NS5a-specific CTL eptitope with the amino acid sequence AQALPVWAR (SEQ ID NO:3) from the HCV NS5a protein. Splenocytes were stained according to Pharmingen's protocol for surface CD8 with peridinin-chlorophyll protein (PerCP)-conjugated anti-mouse CD8 (Pharmingen), and for intracellular IFN-γ and TNF-a with phycoerythrin (PE)-conjugated anti-mouse IFN-γ and TNF-a (Pharmingen). Cells were analyzed on a FACScalibur. The number of events acquired was such that at least 10,000 CD8+ cells were acquired for each sample. Data files were analyzed using the CellQuest software.

Example 7

Demonstration of Sustained Expression of NS5a in the Liver

Animal models are prepared as described in Example 3. The animals can be sacrificed at various time points to confirm expression of the immunogen in the liver using reverse transcriptase-polymerase chain reaction (RT-PCR). Upon sacrifice, tissues are directly frozen in liquid nitrogen prior to grinding. Total RNA is extracted from ground tissue using QIAshredder columns and the RNeasy Kit (Qiagen). First strand cDNA is made using random hexanucleotide primers. PCR is performed using NS5a-specific forward (5'-TGTG-GAGTGGGACCTTCCCC-3' (SEQ ID NO:1)) and reverse (5'-TAGTTCGGCGCAGGAAGGG-3' (SEQ ID NO:2)) primers (which amplify a 70 base pair fragment), under the following conditions: 30 seconds at 94° C. and 45 seconds at 67° C., for a total of 40 cycles. The equivalent of 0.5 μg of RNA is used for each RT-PCR reaction (50 μl). RT-PCR is performed in the presence or absence of RT to ensure that no residual plasmid DNA is amplified. The identity of amplified fragments is confirmed by direct sequencing.

Example 8

Luciferase Assay to Test in Vivo Expression

The luciferase assays are performed as described by Manning et al., supra. Briefly, ground tissue is resuspended into 0.5 ml (muscles and spleens) or 1 ml (livers) of 1× reporter lysis buffer (Promega), vortexed and subjected to three cycles of freeze-thaw. Assays are performed according to Promega's protocol and read on a Dynatech ML3000 plate luminometer (Dynatech, Chantilly, Va.). Total protein concentration in the lysates is determined by BCA (Pierce, Rockford, Ill.) according to the manufacturer's protocol.

Example 9

Screening for Tolerance Modulators

An animal model is prepared according to Example 3. The animal model is then used to screen for agents that break tolerance. A test agent is administered to the animal IV, IM, intraperitoneally (IP) or orally, once or multiple times. A $^{51}$Cr release assay is then performed as described in Example 5 and compared to control animals not receiving the test agent.

Example 10

Screening for Agents that Prevent Tolerance

An animal model, as prepared according to Example 3, is used to screen for agents that prevent tolerance induction by administration of test agents concurrent with the preparation of the animal model. A test agent is administered IV, IM, IP, or orally, once or multiple times, prior to the initial injection of Example 3, or the test agent can be administered at some time point during the process of tolerance induction. A $^{51}$Cr release assay is then performed as described in Example 5 and compared to control animals not receiving the test agent, to determine if the presence of a test agent prevented tolerance induction.

Example 11

Chimpanzee Model of Tolerance to HCV Immunogen

Chimpanzee animal models are established according to protocols similar to those used to establish the mouse tolerance model in Example 3. The same vectors and means of delivery, used for the mouse models, are used in chimpanzees.

Alternatively, chimpanzees that are chronically infected with HCV can serve as models of tolerance to HCV immunogens.

Cells

Intra-hepatic CD8+ T cells are obtained from chimpanzee liver biopsies at different timepoints. Cores of liver, obtained using a 16G Menghini needle, are washed and then gently homogenized in PBS/1% FCS and CD8$^+$ cells affinity extracted using anti-CD8 antibodies bound to magnetic beads as described in Ericson et al., 1993, J. Immunol. 151:4189-4199. Harvesting of CTL cells for bulk analysis and establishmnent of CTL lines is carried out as described in Cooper et al., supra.

Example 12

Demonstration of Induction of Tolerance in Chimpanzee Model Cytotoxicity Assays in Chimpanzees Liver-derived CD8$^+$ cells are tested for cytolytic activity against either autologous, immortalized B cell lines (BLCLs) (which are established as described in Lawlor et al., 1990, Immunol. Rev. 113:147-185) or Patr class I transfectant targets ($5\times10^3$ targets/assay) in standard Na$_2$$^{51}$CrO$_4$ ($^{51}$Cr) release assays. "Patr" is the designation for the common chimpanzee (Pan troglodytes) MHC loci. Patr class I transfectants are established as described in Cooper et al., supra. Varying effector CD8$^+$ cell to target cell ratios (E:T) of from 1 to 20, are assayed. To determine the presence of HCV specificity among expanding CTL lines, initial assays are performed using 100 µl of culture suspension tested against autologous BLCL targets infected with recombinant vaccinia virus (rVV), expressing overlapping regions of the entire HCV polyprotein. The protocol for establishing such rVV constructs can be found in Ralston et al., 1993, J. Virol., 67:6753-6761. Target cells expressing recombinant HCV proteins are infected with rVV at a multiplicity of infection (MOI) of 10 and then labeled with $^{51}$Cr and prepared for assay as described (Erickson et al., supra). When synthetic peptides are tested for ability to sensitize targets for lysis, two approaches are taken depending on the number of different targets: for few targets, cells are coincubated with peptides and $^{51}$Cr (for 1 hour) and then washed (×3) before aliquoting at $51\times10^3$/well; for many targets, cells are $^{51}$Cr-labeled first, then washed and aliquoted, and then incubated with respective peptides for 1 hour before adding CTL. Six to ten micrograms of each peptide is usually incubated with each target, although in some cases up to 30 µg is required for efficient sensitization. Supernatants are harvested after 3 hours, for assays using CTL lines, or 4 hours, for bulk CTL. Percent specific $^{51}$Cr release is calculated: [(Experiment release-Spontaneous release)/(Maximum release-Spontaneous release)] ×100.

Lymphoproliferation Assay (LPA).

Peripheral blood mononuclear cells (PBMCs) are plated in triplicate at $2\times10^5$ cells per well in 96-well round-bottomed plates, and cultured in the presence of, for example, 5 µg/ml recombinant HCV protein or a control. Plates are pulsed with 1 µCi per well of $^3$H-thymidine on day 5, and harvested 6-8 hours later. Results are presented as stimulation index (SI) calculated as (mean experimental cpm)/(mean cpm in the presence of the control protein). SI values of 3.0 or greater are scored as "positive."

Tetramer Staining in Chimpanzee Model

Tolerance can be assessed in chronically HCV infected chimpanzees by comparing the number of HCV-specific cells by tetrameric staining with the number of cells that can actually respond to antigen stimulation (i.e., non-tolerized cells). Tetramer staining protocols, as described in Lechner et al., supra for analysis of HCV-specific human immune cell responses, can be tailored for analysis of HCV-specific chimpanzee immune cell responses.

Many modifications and variations of this invention, as will be apparent to one of ordinary skill in the art, can be made to adapt to a particular situation, material, composition of matter, process, process step or steps, to preserve the objective, spirit and scope of the invention. All such modifications are intended to be within the scope of the claims appended hereto without departing from the spirit and scope of the invention. The specific embodiments described herein are offered by way of example only. The invention is not to be limited by the specific embodiments that have been presented herein by way of example.

I claim:

1. A method for preparing a non-human animal for screening for agents that modulate tolerance to a hepatitis C virus (HCV) immunogen comprising the steps of
preparing a nucleic acid directing liver-specific expression of said HCV immunogen, and
exogenously delivering said nucleic acid to the liver of said animal by portal vein injection, under conditions that result in the sustained expression of the HCV immunogen in the liver thereby inducing immunological tolerance to said HCV immunogen, wherein the HCV immunogen is peptide p214K9 and is expressed for at least one month in said animal.

2. The method of claim 1 wherein the nucleic acid is packaged in an adeno-associated virus particle.

3. The method of claim 1, wherein the animal is a rodent.

4. A non-human animal for screening for agents that modulate tolerance to an immunogen wherein said non-human animal is prepared by the method of claim 1, and wherein said non-human animal is tolerant to said immunogen.

5. A non-human animal for screening for agents that modulate tolerance to a HCV immunogen, said non-human animal prepared by the method of claim 1 wherein said animal is tolerant to said HCV immunogen and wherein said non-human animal is a rodent.

6. A method for preparing a non-human animal for screening for agents that modulate tolerance to a hepatitis C virus (HCV) immunogen, said method comprising delivering a nucleic acid that expresses said HCV immunogen to said animal under conditions that result in the sustained expression of the HCV immunogen in the liver of the animal thereby inducing immunological tolerance to said HCV immunogen, wherein said nucleic acid is not present in the germline of said animal, wherein the HCV immunogen is peptide p214K9, and wherein said p214K9 is expressed for at least one month in the liver of said animal.

7. The method of claim 1, wherein the nucleic acid comprises a liver-specific promoter.

8. The method of claim 7, wherein the liver-specific promoter is an alpha-1 anti-trypsin (AAT) promoter.

9. The method of claim 1, wherein the nucleic acid comprises a liver-specific enhancer.

10. The method of claim 9, wherein the liver-specific enhancer is an apolipoprotein E (ApoE) enhancer.

* * * * *

UNITED STATES PATENT AND TRADEMARK OFFICE
CERTIFICATE OF CORRECTION

PATENT NO.      : 7,638,679 B2  Page 1 of 1
APPLICATION NO. : 09/894845
DATED           : December 29, 2009
INVENTOR(S)     : Xavier Paliard It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 697 days.

Signed and Sealed this

Ninth Day of November, 2010

David J. Kappos
*Director of the United States Patent and Trademark Office*